(12) United States Patent
    Macfarlane

(10) Patent No.: US 8,706,680 B1
(45) Date of Patent: Apr. 22, 2014

(54) AUTOMATED REPORT GENERATION SYSTEM USING A STRUCTURED LEXICON OF ACTIVE LEXEMES AND METHOD

(76) Inventor: Donald E. Macfarlane, Iowa City, IA (US)

( * ) Notice: Subject to any disclaimer, the term of this patent is extended or adjusted under 35 U.S.C. 154(b) by 2090 days.

(21) Appl. No.: 10/907,548

(22) Filed: Apr. 5, 2005

Related U.S. Application Data (60) Provisional application No. 60/559,213, filed on Apr. 5, 2004.

(51) Int. Cl.
  *G06F 7/00* (2006.01)
  *G06F 19/00* (2011.01)
  *G06F 17/30* (2006.01)

(52) U.S. Cl.
  CPC .......... *G06F 19/3487* (2013.01); *G06F 19/363* (2013.01); *G06F 17/30646* (2013.01); *G06F 17/30693* (2013.01)
  USPC .......................................... 707/603; 707/805

(58) Field of Classification Search
  CPC ............ G06F 19/3487; G06F 11/3086; G06F 19/363; G06F 19/345
  USPC ...................... 707/101, 104.1, 603
  See application file for complete search history.

(56) References Cited

U.S. PATENT DOCUMENTS

| | | | | |
|---|---|---|---|---|
| 3,741,471 | A * | 6/1973 | Mani | 235/432 |
| 4,914,590 | A * | 4/1990 | Loatman et al. | 704/8 |
| 5,960,384 | A * | 9/1999 | Brash | 704/9 |
| 6,275,789 | B1 * | 8/2001 | Moser et al. | 704/7 |
| 6,675,159 | B1 * | 1/2004 | Lin et al. | 707/3 |
| 6,684,188 | B1 * | 1/2004 | Mitchell et al. | 705/3 |
| 6,684,276 | B2 * | 1/2004 | Walker et al. | 710/73 |
| 6,801,916 | B2 * | 10/2004 | Roberge et al. | 707/101 |
| 7,181,438 | B1 * | 2/2007 | Szabo | 707/2 |
| 2002/0170565 | A1 * | 11/2002 | Walker et al. | 128/920 |
| 2003/0061072 | A1 * | 3/2003 | Baker et al. | 705/3 |
| 2003/0105638 | A1 * | 6/2003 | Taira | 704/275 |

* cited by examiner

*Primary Examiner* — Hung Q Pham
*Assistant Examiner* — Linh Black
(74) *Attorney, Agent, or Firm* — Ryan N. Carter (57) ABSTRACT

A computer system and database adapted to help with the synthesis and assembly of informational units (lexemes) required for the preparation of professional reports. The system works iteratively, and uses certain characteristics of professional reports to predict which lexemes a user is likely to need at each iteration, allowing the user to select the most useful lexemes from a very large number of lexemes stored in a lexicon for this purpose. The characteristics of professional reports that enable the process of selection include context, predicance and coherence. The report, consisting of an assembly of lexemes, can be exported as text files having different linguistic styles, or as computer code permitting efficient retrieval and computerized analysis of the content of the report for billing, administration, or research.

17 Claims, 8 Drawing Sheets

|   | A | B | C | D |
|---|---|---|---|---|
| 1 | Identifier | Is set by...(predicants) | Query text | Modifier |
| 2 |   |   |   |   |
| 3 |   |   |   |   |
| 4 | 2.0=Med:NewVisit:Complaint | IntMedNew | "Complaint?" |   |
| 5 |   |   |   | Pain |
| 6 |   |   |   | Fever |
| 7 |   |   |   | Tiredness |
| 8 | 6.0=Med:ROS | IntMed | "ROS" | Negative: |
| 9 |   |   |   | Negative in detail: |
| 10 |   |   |   | Positive, |
| 11 |   |   |   |   |
| 12 | 6.40=Med:ROS:CardioResp | InMed, Cardiol, Respiratory | "Cardiorespiratory Sx?" | No symptoms: |
| 13 |   |   |   | Short of breath |
| 14 |   |   |   | Chest pain |
| 15 |   |   |   |   |
| 16 | 6.41=Med:ROS:CardioResp:SOB | Cardiol, Respiratory | "Short of breath?" | None, |
| 17 |   |   |   | Fast walk, |
| 18 |   |   |   | Slow walk, > two blocks. |
| 19 |   |   |   | Slow walk, < two blocks. |
| 20 |   |   |   | At rest, |
| 21 |   |   |   |   |
| 22 | 6.43=Med:ROS:CardioResp:Cough | Cardiol, Respiratory | "Cough?" | None |
| 23 |   |   |   | Dry, |
| 24 |   |   |   |   |

FIG. 2a

| 25 | 6.45=MEd:ROS:CardioResp:ChestPain | Cardiol, Respiratory | | None, |
| --- | --- | --- | --- | --- |
| 26 | | | | |
| 27 | 8.00=Med:PE | IntMed | "Physical Exam" | Not done: |
| 28 | | | | Entirely normal: |
| 29 | | | | Abnormal, |
| 30 | | | | |
| 31 | 8.47=Med:PE:CardioResp:Rhythm | IntMed, Cardiol, Respiratory | "Rhythm?" | Regular, |
| 32 | | | | PVC's |
| 33 | | | | Irreg-irreg, |
| 34 | | | | |
| 35 | 9.22=Test:EKG | EKG | "EKG?" | Not done, |
| 36 | | | | Normal, |
| 37 | | | | A-Fib, |
| 38 | | | | |
| 39 | 10.63=Med:Assessment:Cardiol:Afib | Afib | Afib | New, |
| 40 | | | | Intermittent, |
| 41 | | | | Longstanding |
| 42 | | | | |
| 43 | 13.125=Med:Drug:Anticoagulation | Anticoagulation | "Anticoagulation?" | No, |
| 44 | | | | Warfarin initial, |
| 45 | | | | Warfarin, continued, |
| 46 | | | | Heparin, |
| 47 | | | | |
| 48 | 99.99=END | | | |

FIG.2b

| | E | F | G | H |
|---|---|---|---|---|
| 1 | Sets... (predicants) | Action | Style 1 | Style 2 |
| 2 | | | &&3x5 card: Shorth ead& | &&HeadedNotePaper:HPHeader& |
| 3 | | | | |
| 4 | | Loop PainQuestionnaire | | The patient's chief complaint was pain. |
| 5 | Infection, Fever | | CC: Fever | The patient's chief complaint was fever. |
| 6 | | Loop TirednessQuestionnaire | | The patient's chief complaint was tiredness. |
| 7 | | | | |
| 8 | | | ROS -ve | The Review of Systems was negative |
| 9 | | | ROS -ve | Review of Systems: The patient denied constitutional, head and neck, cardiorespiratory, abdominal, genito-urinary, dermatologic, rheumatologic, neurologic, or psychiatric symptoms. |
| 10 | | | ROS: | Review of Systems: |
| 11 | | | | |
| 12 | | | nSOB, cCP, nCough | No shortness of breath, chest pain or cough |
| 13 | Cardiol, Respiratory | | | |
| 14 | Cardiol | | | |
| 15 | | | | |
| 16 | | | nSOB | [He] denied shortness of breath |
| 17 | EKG, Oxygen, CXR | Loop SymptomDuration | SOB fast walk | [He] admitted to shortness of breath only on fast walking shortness of breath |

FIG.2c

| | | | |
|---|---|---|---|
| 18 | EKG, Oxygen, CXR | Loop SymptomDuration | SOB > 2bl | [He] had shortness of breath but only after walking more than two blocks |
| 19 | EKG, Oxygen, CXR | Loop SymptomDuration | SOB < 2bl | [He] is short of breath after walking two blocks |
| 20 | EKG, Oxygen, CXR | Loop SymptomDuration | SOB @ rest | [He] has shortness of breath at rest. |
| 21 | | | | |
| 22 | | | nCough | [He] does not have cough |
| 23 | | | +Dry cough | [He] has a dry cough |
| 24 | | | | |
| 25 | | | | |
| 26 | | | | |
| 27 | | | | No physical exam was performed at this visit |
| 28 | | | PE -ve | The physical exam was entirely normal |
| 29 | | | PE: | Physical exam: |
| 30 | | | | |
| 31 | | | RRR | The pulse had regular rate and rhythm |
| 32 | | | PVC's | The pulse revealed occasional premature ventricular contractions |
| 33 | EKG | | IregIreg | The pulse was irregularly irregular. |
| 34 | | | | |
| 35 | | | | |
| 36 | | | EKG nl | The electrocardiogram showed sinus rhythm and no evidence of ischemia |
| 37 | | | EKG A-fib | The electrocardiogram showed atrial fibrillation |
| 38 | | | | |

FIG.2d

| | | | |
|---|---|---|---|
| 39 | Anticoagulation, cardioversion | New a-fib | [The patient] has a recent onset of atrial fibrillation |
| 40 | Anticoagulation, cardioversion | Int a-fib | [The patient] has intermittent atrial fibrillation |
| 41 | Anticoagulation, cardioversion | Old a-fib | [The patient] has long standing atrial fibrillation |
| 42 | | | |
| 43 | | | We elected not to anticoagulate [him] |
| 44 | Drug:Anticoagulation:Warfarin<br>Do PrintWarfarinAdvisory;<br>Do ReferToAnticoagClinic | Start warfarin | We advised [him] about the risks and benefits of anticoagulation, and [he] agreed to start warfarin. |
| 45 | Drug:Anticoagulation:Warfarin<br>Do SendFileAnticoagulation Clinic | Cont warfarin | We advised [him] to continue to take warfarin |
| 46 | | | |
| 47 | Close File, Print Document, | | |
| 48 | EXIT | | |

FIG.2e

AUTOMATED REPORT GENERATION SYSTEM USING A STRUCTURED LEXICON OF ACTIVE LEXEMES AND METHOD

BACKGROUND OF THE INVENTION

The present invention is directed to a system and method for generating reports using computer algorithms that enable the user to provide a means of finding the most suitable fragments of information (lexemes) stored in a library (lexicon) for inclusion in the report, and to prepare the report in a variety of formats.

In the course of their practice, many professionals generate a variety of written reports. Preparing these reports is labor intensive, and this labor is largely redundant if these reports contain passages similar to previously prepared reports. The information in reports is used for a variety of purposes, some of which require elegant language, some permit abbreviations, and some (such as billing) are best performed by abstracting the report into computer code. Because of the incompatibility of elegant language and computer code, abstracting is often carried out by hand, which is both error-prone and inefficient.

The need for a variety of reports is especially true in the field of medicine, which requires practitioners to generate both highly complex reports and extremely detailed billing instruments. To this end, modern word processors have limited capacity to complete a word or simple phrase after a few characters have been entered. Inserting appropriate boilerplate text using a conventional word processor is valuable if the transaction is simple and can be accommodated by handful of suitable paragraphs. However, many professions deal with highly complex scenarios that call for subtle variations of language which might aggregate to millions of phrases which cannot be stored and recalled usefully by a word processor.

Another method for capturing the information produced during a patient encounter for inclusion in a written report is for the physician to prepare the report by hand or use dictation. Report generation using this method may take five to ten minutes per patient encounter, so that the typical half-day clinical session requires at least one hundred minutes of time by the physician, and generates a report that cannot be usefully examined in any detail by computer.

Therefore, there is a need for a computer program that can suggest to the user fragments of information that are appropriate for inclusion in a document wherein the information can be presented in a number of styles, including forms amenable to computerized storage, analysis, and retrieval.

SUMMARY OF THE INVENTION

The present invention is a computer system adapted to help with the generation and organization of the informational units required in professional reports. The system incorporates algorithms that have the capacity repeatedly to offer to the user a menu of a handful of informational units (lexemes) that the user is likely to need from a library (lexicon) containing a very large number of phrases. Users can either select one of the offered lexemes, or add their own text, which may subsequently be added to the lexicon. When the selection is made, the system will append the selected lexeme to the output file, and move on to display another menu of lexemes. Since lexemes can be represented as language or code, the information in the completed report can be as a document in a number of styles or as computer code amenable to retrieval. This process is reiterated until the document is completed.

The information in the report can be presented in a number of linguistic styles, including coded data amenable to computerized storage, analysis, and retrieval.

The value of the system of the present invention extends far beyond relieving users of the repetitive tasks of report generation. The report that is generated is structured and codified is such a way that the information contained in the report is easily manipulated by computers. The system will permit cross platform compatibility of medical records. Medical records generated by the present invention will consist of a list of lexemes. This list will be quite compact, and it can easily be stored on a small device, such a "smart" card that can be retained by the patient. Third parties can easily provide their own translation of lexemes within the lexicon to enable them to import and manipulate data generated in a proprietary fashion.

BRIEF DESCRIPTION OF THE DRAWING

FIG. 1b is a continuation of the flow chart of FIG. 1a;
FIG. 2b is a continuation of the spread sheet shown in FIG. 2a;
FIG. 2c is a continuation of the spread sheet shown in FIG. 2a;
FIG. 2d is a continuation of the spread sheet shown in FIG. 2a;
and
FIG. 2e is a continuation of the spread sheet shown in FIG. 2a.

DESCRIPTION OF THE PREFERRED EMBODIMENT OF THE INVENTION

The present invention consists of a computer program termed a system or lexeme editor, which has access to one or more lexicons storing a multitude of lexemes. The program is adapted for use with a computer and all of the computer's parts and accessories, including a processor, a data input interface such as a keyboard, digitizing tablet etc, and a data output interface such as a monitor. Although the invention is described herein primarily for use in the medical field, it should be noted that the invention can be used for the generation of any report or document.

The smallest unit of communication roughly corresponds with a phrase of language. It is useful to separate the informational content of a phrase from the language that is used to express it. The informational content disembodied from its language is referred to as a lexeme, which is defined as the information contained within the smallest intelligible unit of communication. Just as words are collected in a dictionary, lexemes may be collected into a lexicon.

In order to address how to construct a suitable computer program and lexicon library, the Applicant has examined how language is used in professional reports. It has been determined that there are four characteristics of professional reports that can be used to predict the text that the professional is likely to need when preparing a report. These characteristics are termed context, predicant, coherence, and style. Each of these characteristics is described below in turn.

Context is defined as the information that is available prior to the professional interaction with the patient or client. To a substantial extent, the form and outline of a report is determined by the context in which it is created. This context may include the location in which the interaction occurs, the identity of the subject, and the specialization of the professional. For instance, a report generated by a pediatrician seeing a child with earache is predictably very different than that created by a cardiologist performing a cardiac catheterization. Information about the context might be gathered from pre-existing computer files such as the patient demographic information and the clinic schedule. Prior reports concerning the patient may contribute to the context. For instance if a prior report indicates that the patient has diabetes, subsequent reports will predictably include information with respect to diabetes. The context will determine the general layout of the report, and it will set a number of variables and predicants that can be used later by the editor. Examples of the variables include the identity of the lexicon to be used, the type of note paper to be used, the general layout of the document, the date, identity of the client and the professional, the location and the nature of the interaction.

Much of the content of later portions of a document can be predicted by the content of earlier portions. These predictive contents are referred to as predicants. For instance, a physician seeing a patient who complains of severe headache is likely subsequently to record whether or not the patient has nausea with the headache and to examine whether the neck is stiff. If the patient has knee pain, the physician is likely to ask about the knee locking and examine the knee for excess fluid. A radiologist finding a mass on a chest radiograph of a smoker is likely to comment on the characteristics suggesting that the mass is a cancer. The easiest predicants to understand are diagnoses, but predicants are more powerful than that. Predicants can be elements of the history (such as symptoms) or abnormalities found during the physical exam that call for further analysis within the text.

In one embodiment, predicants are abbreviations of conditions that are set to be true by the context, or which become true as the session with the user progresses. In one embodiment, the predicants are stored as a simple predicant list by the system. The predicant list therefore includes all the predicants that are set to be true at the time, and this list increases in number during the session with the user.

All documents tend to be subdivided into sections, paragraphs, sentences and phrases. In professional documents these subdivisions tend to follow a predetermined order which is called coherence. For instance, in a typical medical record, the section "history of the present illness" is placed before the section "physical exam." Coherence may be imposed on the user by explicit rules, but it is more likely that the rules of coherence arise by custom, conforming to the expectation of both the author and reader. The lexicon stores lexemes with information necessary to place all the lexemes in coherent order.

In the course of their work, professionals generate reports in a number of different styles. The information within a report can be expressed in different linguistic styles, each of which may serve a different purpose. One style might be a brief note in an office medical chart that makes extensive use of abbreviations and symbols rather than full sentences. The same factual information can be recast in the form of a full letter replete with the usual courtesies to be sent to a referring physician. The identical factual information might be codified and loaded into a computer database for archival, billing or management purposes. Each of these documents may contain the same information, but they differ radically in their style.

The concept of the lexeme can be combined with the above described principles of coherence, context, predicant, and style to make several general statements about lexemes. First, the principle of coherence enables the determination of where any lexeme should be positioned within a report. Second, in general, only one lexeme can be selected for use in one coherent location in the record. For instance, there can be only one lexeme reporting a patient's left knee jerk. Third, the likelihood that the author will elect to use a particular lexeme in the course of creating the report can be predicted from the context and predicants. Fourth, the fact that the user selects a lexeme (and its modifiers) may contribute one or more predicants that can be used for the remainder of the report. Finally, the style of the document indicates how the lexeme will be expressed linguistically in the report.

As discussed above, lexemes are units of information. Within the context of report writing, the fact that a user has selected a lexeme along with its modifier for inclusion in the text is likely to be a predicant that can be used to predict which lexemes the user might wish to use later in the document. We take advantage of this implication by storing with the lexeme in the lexicon one or more instructions to be executed by the system. Lexemes that initiate actions when they are selected are referred to as active lexemes. Active lexemes can include instructions to the system, such as adding predicants to the predicant list (defined above), or moving forward to the next paragraph or section of the report. Some active lexemes may not have language associated with them, rather they consist only of commands concerning the layout of the report or how it is to be printed or saved. Other active lexemes might initiate a complex series of instructions, such as preparing an informational booklet for a patient describing the chemotherapy they are planning to receive. Active lexemes could also import segments of text from previously prepared documents, such as copying the past medical history of a patient from another source. Active lexemes can set variables, and set or reset flags, which may subsequently be used by the editor.

Figure 1A:
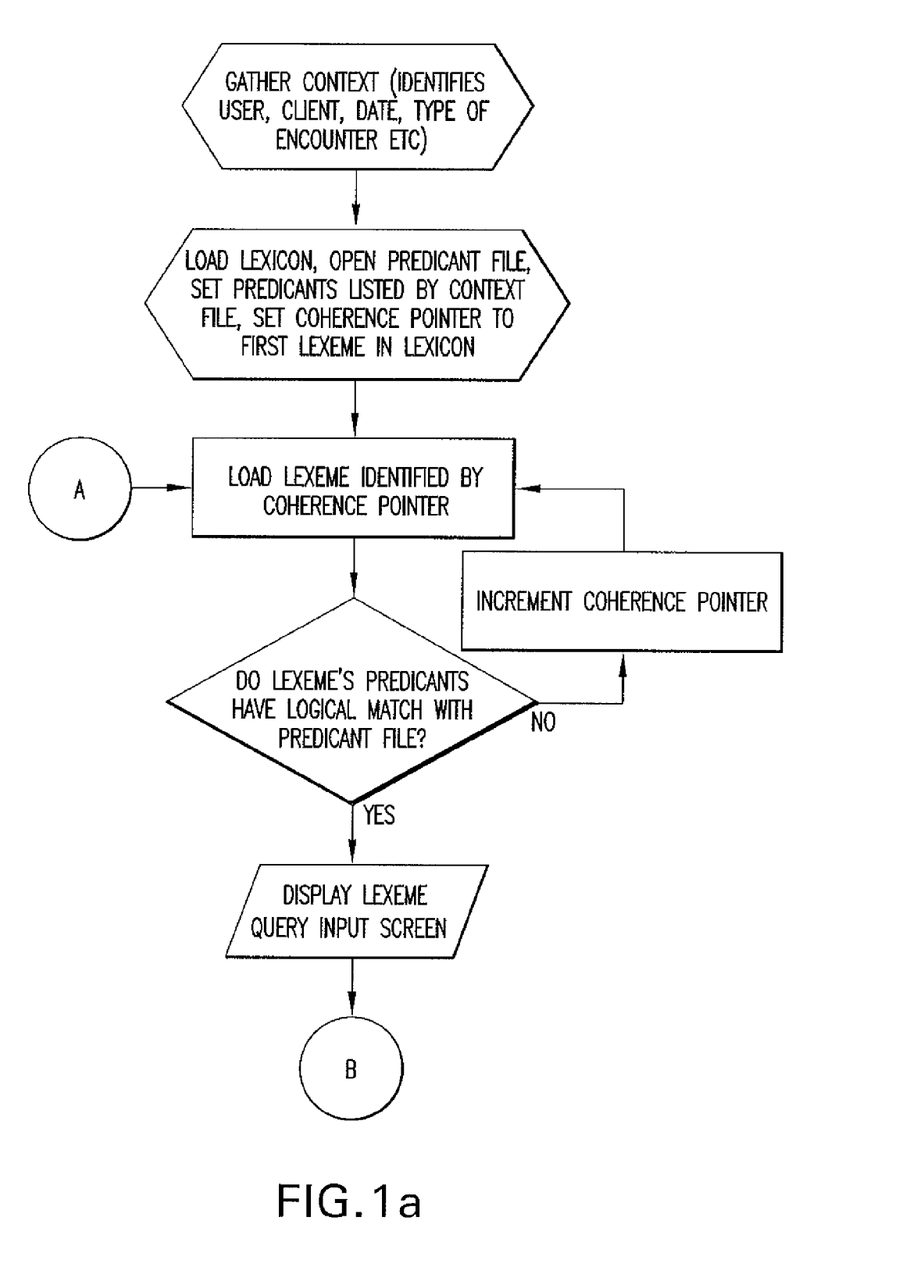
FIG. 1a is a flow chart showing the preferred steps of the present invention.
Figure 1B:
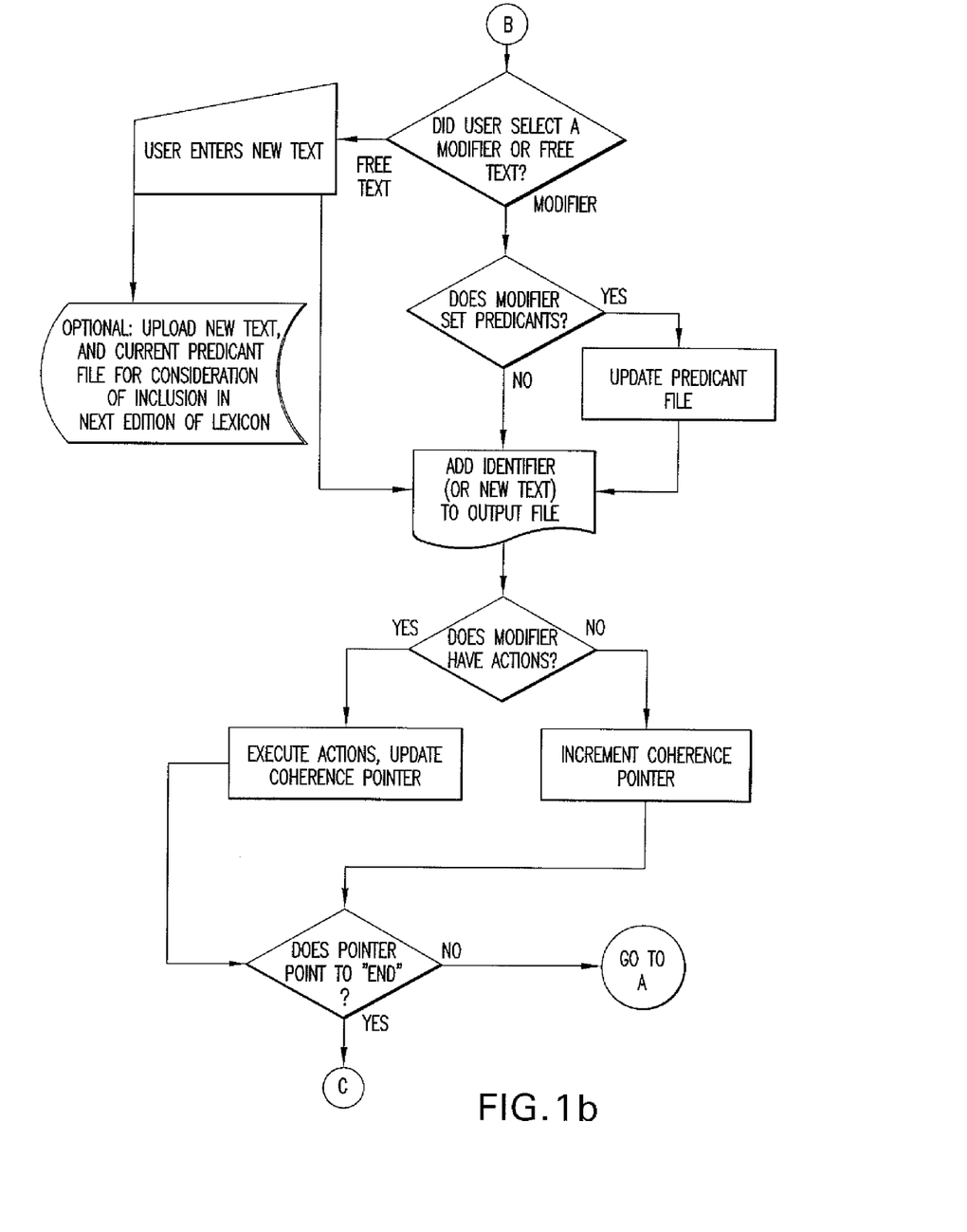
Figure 1C:
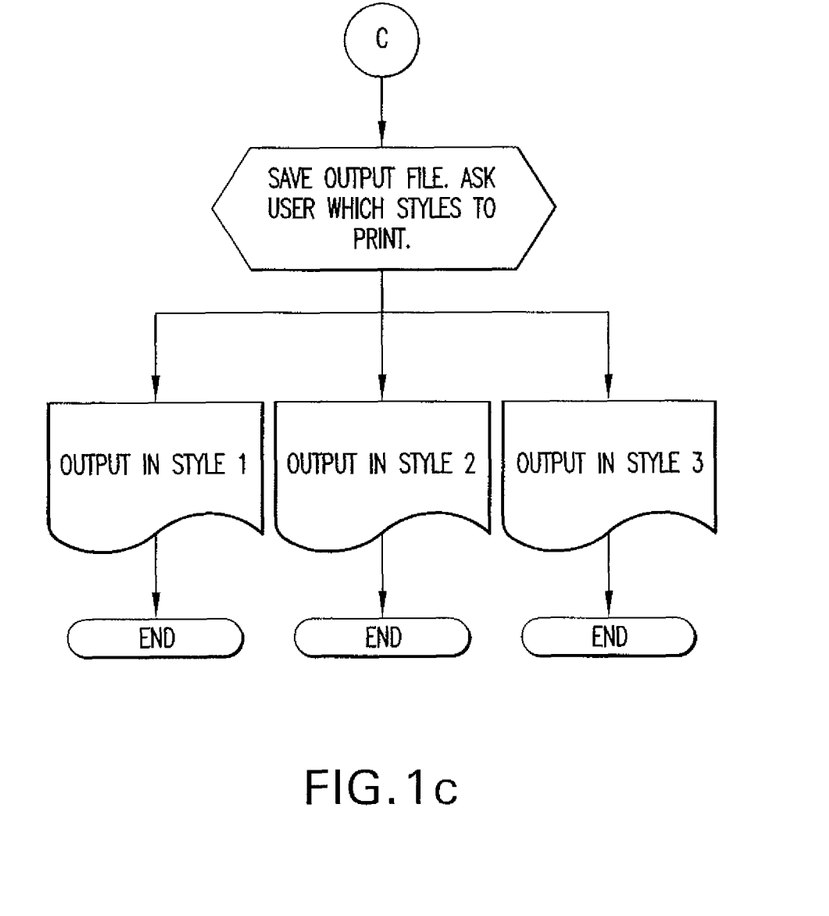
FIG. 1c is a continuation of the flow chart of FIG. 1b.
Figure 2A:
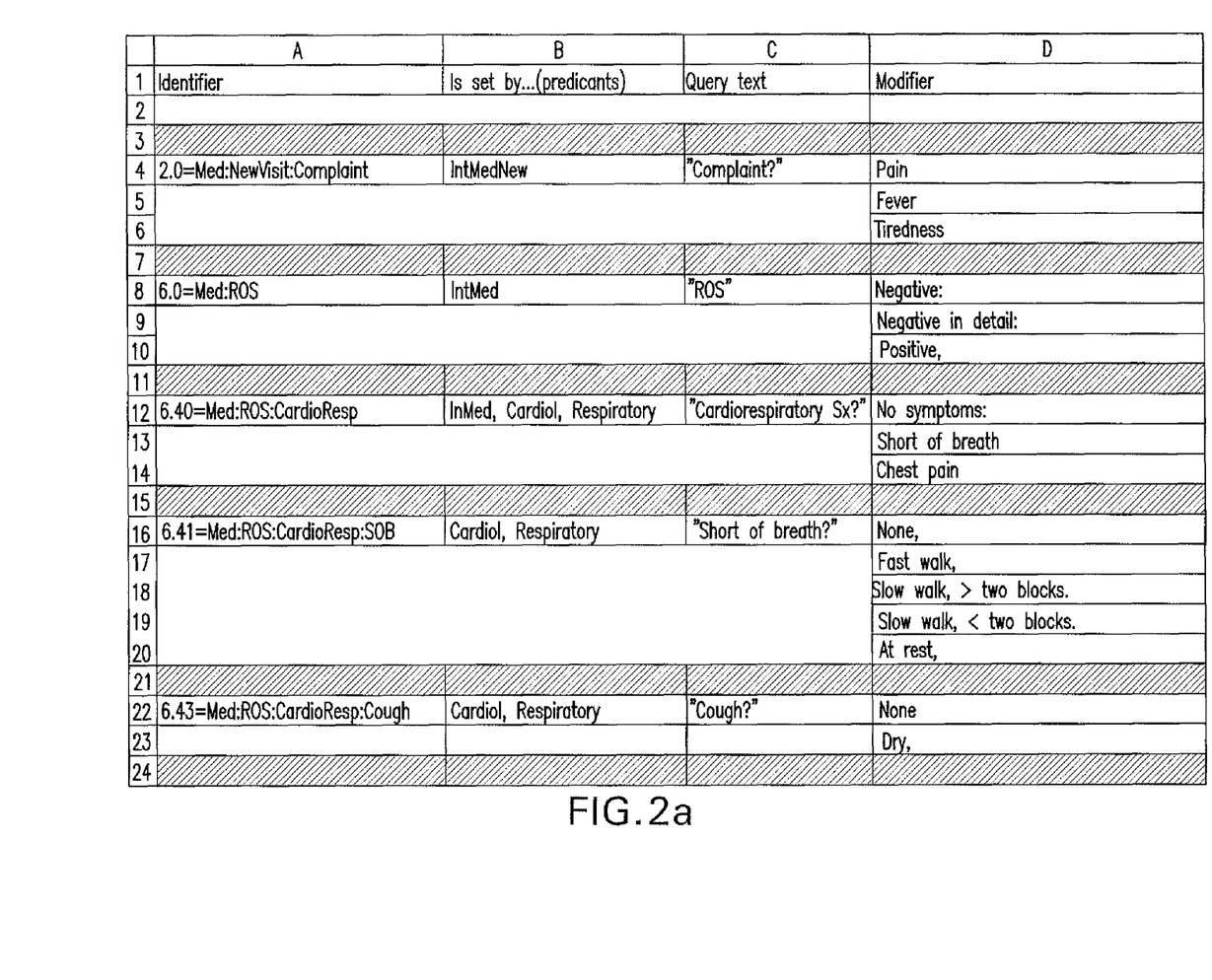
FIG. 2a is a spread sheet showing an illustrative example of the present invention.
Figure 2B:
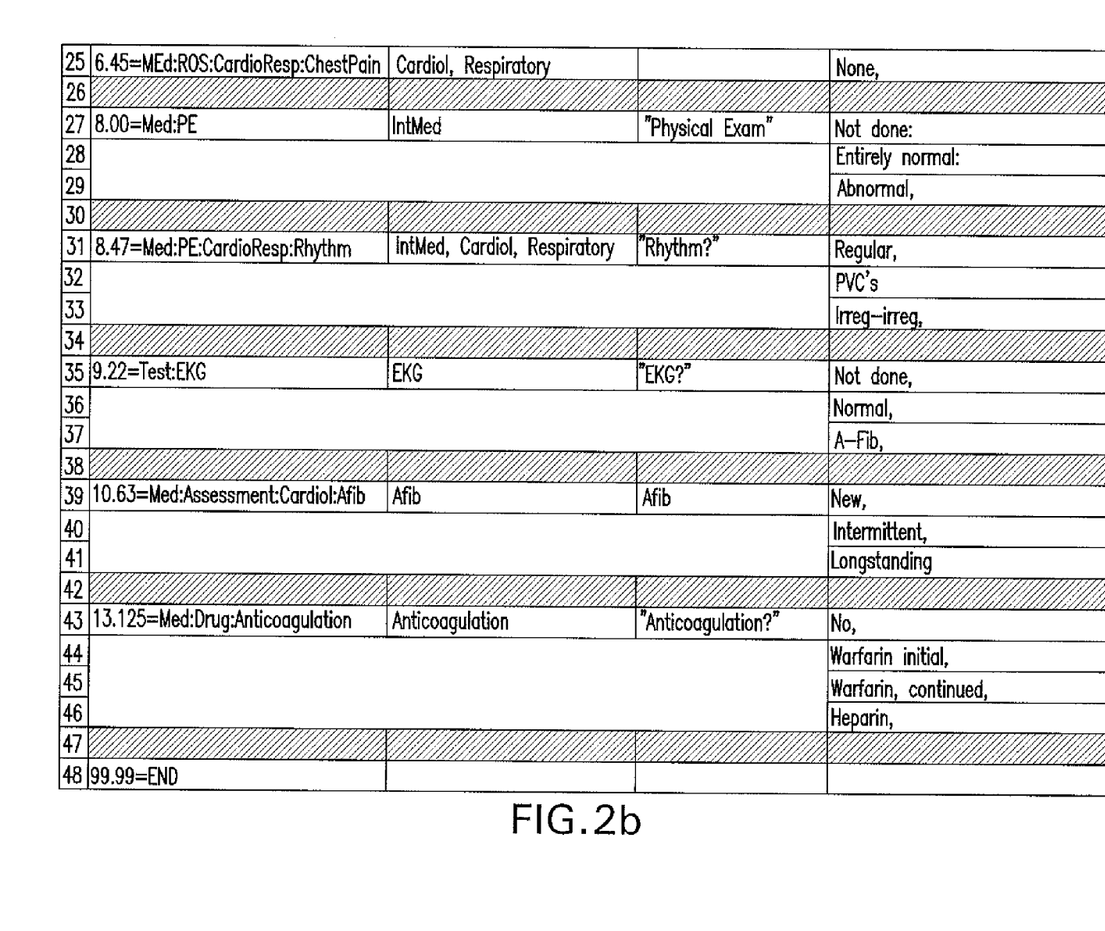
Figure 2C:
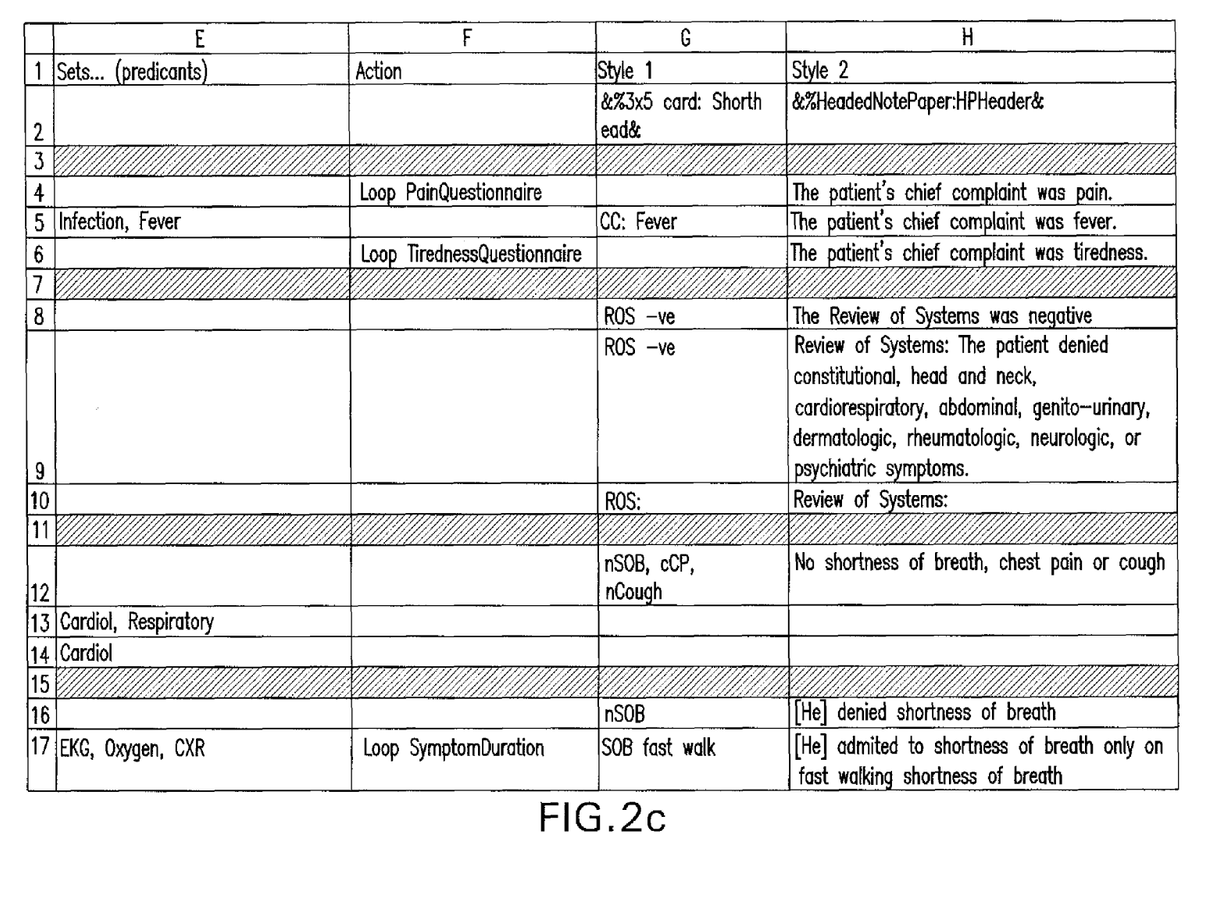
Figure 2D:
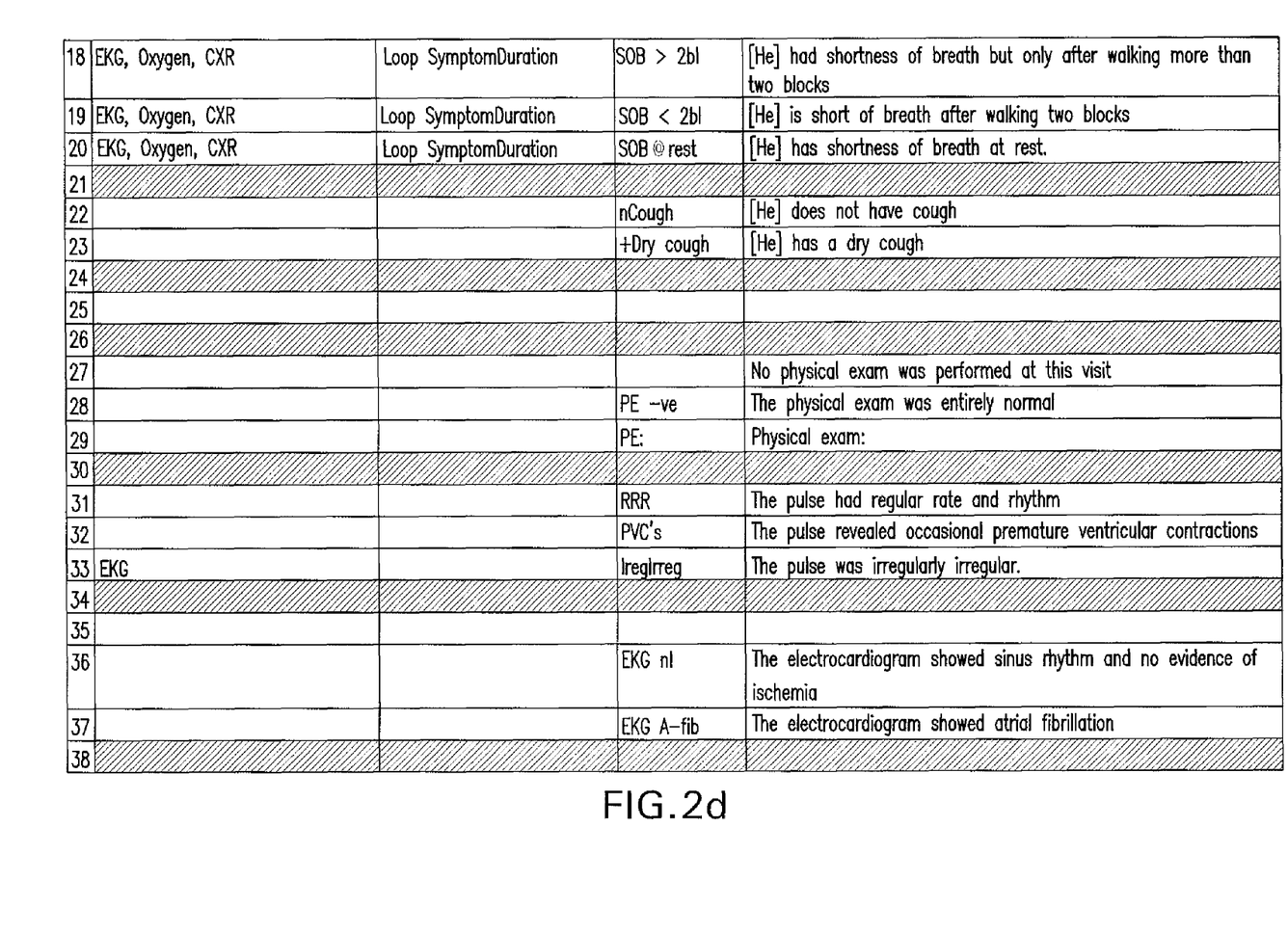
Figure 2E:
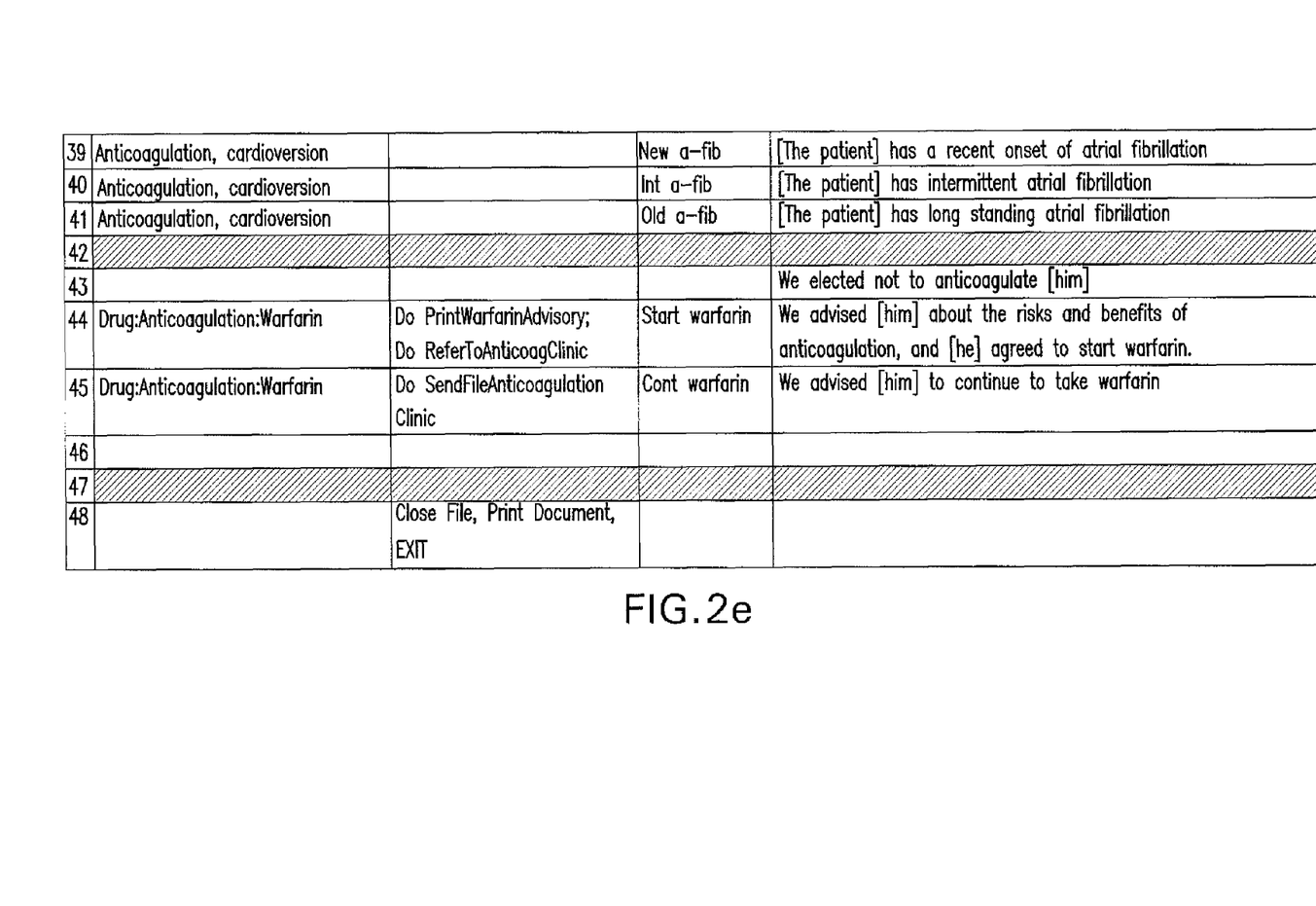

FIGS. 1a, 1b, and 1c shows a flow chart of how the present invention works. The context is used to set the values of variables, such as the client's name, and to add some predicants to a predicant list. At each iteration of the system, it displays for the user one or more lexemes and modifiers, from which the user makes selections. Once the selection is made, the system exports the identity of the selected lexemes to be concatenated to the output file. The system also adds any predictants that are set by the lexeme to the predicant list, and examines whether the lexeme instructs the system to move forward to the level (e.g. the next section or paragraph) of the report. The system also carries out any special instruction within the lexeme (active lexeme).

The system then seeks the next lexeme query in the coherence order within the lexicon that is at the right level (i.e. paragraph or section), and which contains predicants that match any of those on the predicant list. The effect of this is to repeatedly offer to the user lexeme queries which are timely within coherence, and which invite the user to address issues pointed to by the predicant list.

The lexicon consists of all of the lexemes that might be needed for the creation of a document. The number of lexemes in a lexicon may be hundreds of thousands. At first sight, it might seem difficult to compile a list of these lexemes, but this task can largely be automated. A first draft of a lexicon is prepared by hand, after examining several existing examples of the document. This first draft of the lexicon can be used by the system. When early users need lexemes that are not found in the first draft, they will enter the new lexemes and modifiers into the lexicon. The system will save user-entered new lexemes in a file, together with the current coherence, context and predicant information. In the preferred embodiment, the contents of this file will automatically be submitted to a central editorial office, which will incorporate the suitable new lexemes in subsequent editions of the lexicon. The newly suggested lexeme will be communicated to the editorial office together with the prevailing predicant list and coherence information. This information will be used by the editorial office to attach this appropriate information to the active lexeme prior to its publication, if the user is not sophisticated enough to complete these tasks.

FIGS. 2a, 2b, 2c, 2d, and 2e show exemplary spread sheets which contain a handful of the thousands of lexemes that might be used with a hypothetical patient. In this illustration, each lexeme occupies one full line of the spreadsheet (lines 4, 8, 12, 16, 22, etc. . . . ), with additional lines to accommodate its modifiers. Lexemes are generally entered into the lexicon in coherence order, but lexemes that constitute subroutines (or loops) are listed separately. In this example, lexemes are entered in hierarchies: lexemes with higher number of colons in the identifier are nested within the hierarchy of lexemes having a lower number of colons. This example contains only a few illustrative fragments of the complete interaction.

Column A identifies the lexeme. The terms "ROS" means "review of systems," and "PE" means "physical exam." Column B contains a list of predicants. The editor will perform a logical comparison of the content of this predicant file to the contents of this cell, and if not match is found, the editor will skip over the lexeme. Column C contains the text that will be displayed by the editor as the query, prompting the user to respond.

Column D contains the modifiers (which may also be referred to as responses since they are responsive to the lexeme query presented to the user). The editor presents these modifiers to the user as acceptable responses to the query. In this implementation, modifiers are followed by punctuation. The absence of punctuation permits the user to make more than one selection (e.g. lines 4, 5, and 6). A terminal comma permits one selection only (lines 16-20). The colon indicates that selecting the modifier terminates the current hierarchy of lexemes, forcing the editor to skip to the beginning of the next block of the same level (lines 8-9). A period (not shown) instructed the editor to skip to the beginning of a block one level senior to the current level.

Column E has the changes that are to be made to the editor's predicant file if the modifier is selected by the user. These changes are most likely to be additions to the predicant file, but deletions may occur. Column F contains a list of actions to be carried out by the editor if the modifier is selected. Actions may include navigation instructions, such as performing a subordinate block of lexemes (e.g. lines 4 and 6), performing a housekeeping function (lines 2 and 48), or preparing an additional document (lines 44 and 45).

Columns G and H contain the fragments of output text in two different styles that the editor may issue. In practice, the lexicon is likely to contain several such columns each with its own style. These outputs are a mixture of text and printing or file storage instruction that on completion of the session are concatenated and which can be sent to a printer, or sent to a file repository, word processor, fax, e-mail program, or legacy system. The two styles shown in this example are a 3 by 5 inch card using abbreviations, and a more verbose style printed on headed notepaper (line 2).

The hypothetical patient is identified during the acquisition of the context as a patient needing a history and physical exam as a new patient in the Internal Medicine clinic. The Context sets the predicant, IntMedNew, and IntMed. This prompts the query "Complaint?" as shown in Column C. The physician selects the response "Tiredness" which diverts the flow to a subroutine consisting of a tiredness questionnaire (not shown).

During the review of systems, the physician selects line 10, then line 13 short of breath. This sets the predicants "Cardiol" and "Respiratory", leading to the shortness of breath query starting on line 16. The response is line 18 (short of breath after 2 blocks walking), setting the predicants EKG (cardiogram), Oxygen (evaluating the need for therapy with oxygen), and CXR (chest X-ray).

During the physical exam, the physician finds that the pulse is irreg-irreg (indicated by selecting line 33). He reads the EKG as showing atrial fibrillation (line 39). Atrial fibrillation can be corrected by cardioversion, and it is generally wise to give blood thinners prior to cardioversion to prevent blood clots forming in the heart that can fly off and cause stroke. For this reason, selecting atrial fibrillation sets the predicants Anticoagulation and Cardioversion. The effect of selecting warfarin (line 44) results in the printing of a personalize pamphlet for the patient describing the risks and benefits of warfarin, and initiating a referral of the patient to the Anticoagulation Clinic. At the end of the transaction, the predicant file includes: IntMedNew, IntMed, Cardiol, Respiratory, EKG, Oxygen, CXR, Afib, Anticoagulation, Cardioversion, Drug: Anticoagulation: Warfarin.

The value of the system of the present invention extends far beyond relieving users of the repetitive tasks of report generation. The report that is generated is structured and codified is such a way that the information contained in the report is easily manipulated by computers. The most powerful application of our system occurs in medicine. The cost of creating and maintaining medical records is huge, and the records that are created need to be read by sophisticated personnel to justify expenditures and reimbursement. With rare exceptions, medical record systems are incompatible with each other. As a result, health care administration and health services research often requires detailed reading of medical charts on site or after copying.

The system will permit cross platform compatibility of medical records. Medical records generated by the present invention will consist of a list of lexemes. This list will be quite compact, and it can easily be stored on a small device (such a "smart" card). To import and manipulate data generated by the present invention, all that third parties will need to do to is to append their own translation of lexemes to our lexicon. The system will then convert the list of lexemes into language meeting the third party's requirements. These requirements might include criteria needed for reimbursement. Lexemes do not need to include the patient's identity, so medical records can be stored centrally and aggregated for research purposes without fear of compromising confidentiality. Patients may elect to have their medical records stored in a central repository using an encrypted identifier. Cross platform compatibility will enormously reduce the cost and complexity of third party reimbursement. Indeed, it is reasonable that processing a medical bill using the system tomorrow may be as fast as processing a credit card payment today.

Having thus described the invention in connection with the preferred embodiments thereof, it will be evident to those skilled in the art that various revisions can be made to the preferred embodiments described herein with out departing from the spirit and scope of the invention. It is my intention, however, that all such revisions and modifications that are evident to those skilled in the art will be included with in the scope of the following claims.

What is claimed is:

1. An automated method that enables a user to prepare a report using a computer system having a processor, an input interface, and an output interface, said method comprising:
   entering context information into the input interface;
   displaying a single lexeme query and associated lexeme responses from a lexicon containing a plurality of such queries and associated responses on the computer system's output interface;
   allowing the user to select a response to the lexeme query from the display wherein the queries are displayed iteratively one-at-a-time in an order established by the system's coherence and predicance, and wherein the user is constrained to respond to the queries in the order they are presented by the system;
   determining whether the selected lexeme response instructs the system to move forward to the next section of the report, and if so, moving the system forward to the next section of the report;
   determining whether the selected lexeme is an active lexeme, and if so, executing the task associated with the active lexeme;
   determining whether the selected lexeme sets new predicants to be true, and if so, adding the predicants to a predicant list stored by the system;
   determining the next lexeme query in the order established by the coherence of the lexicon which contains one or more predicants matching the current predicant list and displaying this next lexeme query on the computer system's output interface;
   iterating this process until the report is complete; and
   concatanating and exporting the content of the selected lexeme responses in one or more styles.

2. The method of claim 1 wherein the system chooses to display lexeme queries and responses based on context information.

3. The method of claim 2 wherein the system displays lexeme queries and responses only if there is at least one match between the predicants stored with the lexeme query and the current predicant list.

4. The method of claim 3 wherein the context information sets at least some of the predicant information.

5. The method of claim 1 wherein the system chooses to display lexeme queries and responses based on coherence information.

6. The method of claim 1 wherein the lexeme query is displayed in the form of a question.

7. The method of claim 1 further comprising the step of entering text into the report manually.

8. The method of claim 7 wherein the text is automatically submitted to a central editorial office for consideration of incorporation in subsequent lexicons.

9. The method of claim 1 wherein the report can be printed in one or more styles.

10. The method of claim 1 wherein the report can be electronically stored in one or more styles.

11. The method of claim 1 wherein the report can be electronically transmitted in one or more styles.

12. A system for generating a report whereby a user selects a response from a plurality of lexeme responses in response to a lexeme query, said system comprising:
   a processor;
   an input interface configured to receive data input from the user and an output interface coupled to said processor;
   a memory;
   a lexicon comprising of a plurality of lexeme queries and associated responses stored in said memory which lexeme queries and associated responses are accessible by said processor;
   wherein said user interface is configured to receive context information from the user which is processed to determine which lexeme query to display on the output interface;
   wherein the user is able to select the desired response using the input interface; and
   wherein the system determines which lexeme query and associated responses to display based on context, predicance, and coherence; wherein the queries are displayed iteratively one-at-a-time in an order established by the system's coherence and predicance; and
   wherein the user is constrained to respond to the queries in the order they are presented by the system.

13. The system of claim 12 wherein the system further comprises at least one response—which relates to the displayed lexeme query.

14. The system of claim 12 wherein the system is adapted to print, send, and store information in a variety of styles.

15. The system of claim 12 wherein the lexeme query is presented on the output interface in the form of a question.

16. A system for generating a report for a user, said system comprising:
   a processor;
   an input interface configured to receive data input from a user and an output interface coupled to said processor;
   a memory;
   a lexicon having a plurality of sections, each section having a plurality of entries constructed in coherence order, wherein each entry of the lexicon comprises:
      a lexeme query associated with one or more predicants, wherein at least one predicant must match a predicant list stored in the system for the system to select the lexicon entry to be presented to the user;
      displayable information associated with the lexeme query that prompts the user to address the subject matter of the entry;
      one or more lexeme responses which, when selected by the user, will cause the system to export the associated lexeme in one or more styles, add any associated predicants to the current predicant list, execute any associated actions, and execute any instruction to move the system forward to the next section of the lexicon in coherence order;
   wherein the queries are displayed iteratively one-at-a-time in an order established by the system's coherence and predicance; and
   wherein the user is constrained to respond to the queries in the order they are presented by the system.

17. A computer program product, comprising a computer usable medium having a computer readable program code embodied therein, said computer readable program code adapted to be executed to implement a method for generating a report, said method comprising:
   a computer system having a processor, an input interface, and an output interface;
   entering context information into the input interface;
   displaying a single lexeme query and associated lexeme responses from a lexicon containing a plurality of such queries and associated responses on the computer system's output interface;
   allowing the user to select a response to the lexeme query from the display wherein the queries are displayed iteratively one-at-a-time in an order established by the system's coherence and predicance, and wherein the user is constrained to respond to the queries in the order they are presented by the system;

determining whether the selected lexeme response instructs the system to move forward to the next section of the report, and if so, moving the system forward to the next section of the report;

determining whether the selected lexeme query is an active lexeme, and if so, executing the task associated with the active lexeme;

determining whether the selected lexeme sets new predicants to be true, and if so, adding the predicants to a predicant list stored by the system;

determining the next lexeme query in the predetermined order established by the system's coherence within the lexicon which contains one or more predicants currently set to true and displaying that next lexeme query on the computer system's output interface;

iterating this process until the report is complete; and exporting the selected lexeme responses in one or more styles.

* * * * *